United States Patent [19]

Goldfarb et al.

[11] Patent Number: 5,155,217

[45] Date of Patent: Oct. 13, 1992

[54] ONGOGENE ENCODING POLYPEPTIDE HAVING GROWTH FACTOR ACTIVITY

[75] Inventors: Mitchell Goldfarb, River Edge, N.J.; Xi Zhan, New York, N.Y.

[73] Assignee: The Trustees of Columbia University in the City of New York, New York, N.Y.

[21] Appl. No.: 56,137

[22] Filed: May 29, 1987

[51] Int. Cl.$^5$ ............................................. C12N 15/18
[52] U.S. Cl. ........................................ 536/27; 935/13
[58] Field of Search .................. 435/68, 70, 91, 172.3, 435/317.9, 320, 6, 7; 935/6, 13, 19; 526/227

[56] References Cited

PUBLICATIONS

Sakamoto et al., (1986) Proc. Nat'l Acad, Sci. 83: 3997–4001.
Taira et al., (1987) Proc. Nat'l Acad., Sci. 84: 2980–2984.
Abraham et al., (1986) Science 233: 545–548.
Fogh et al., (1977) J. Nat. Cancer Inst. 59:221–225.
Abraham, J. A., et al., *Science*, vol. 233, pp. 545–548 (1986).
Moore, R., et al., *EMBO Journal*, vol. 5, pp. 919–924 (1986).
Taira, M., et al., *Proc. Natl. Acad. Sci. U.S.A.*, vol. 84, pp. 2980–2984 (1987).
Shih, C., et al., *Proc. Natl. Acad. Sci. U.S.A.*, vol. 76, pp. 5714–5718 (1979).
Perucho, M., et al., *Cell*, vol. 27, pp. 467–476 (1981).
Murray, M., et al., *Cell*, vol. 25, pp. 355–361 (1981).
Krontiris, T. G. and Cooper, G. M., *Proc. Natl. Acad. Sci. U.S.A.*, vol. 78, pp. 1181–1184 (1981).
Pulciani, S., et al., *Nature*, vol. 300, pp. 539–542 (1983).
Yuasa, Y., et al., Nature, vol. 303, pp. 775–779 (1983).
Parada, L. F., et al., *Nature*, vol. 297, pp. 474–478 (1982).
Santos, E., et al., *Nature*, vol. 298, pp. 343–347 (1982).
Der, C. J., et al., Proc. Natl. Acad. Sci. U.S.A., vol. 79, pp. 3637–3640 (1982).
Shimizu, K., et al., *Proc. Natl. Acad. Sci. U.S.A.*, vol. 80, pp. 2112–2116 (1983).
Hall, A., et al., *Nature*, vol. 303, pp. 396–400 (1983).
Shimizu, K., et al., *Proc. Natl. Acad. Sci. U.S.A.*, vol. 82, pp. 5641–5645 (1985).
Fukui, M., et al., *Proc. Natl. Acad. Sci. U.S.A.*, vol. 82, pp. 5954–5958 (1985).
Eva, A. and Aaronson, S. A., *Nature*, vol. 316, pp. 273–275 (1985).
Martin-Zanca, D., et al., *Nature*, vol. 319, pp. 743–748 (1986).
Dean, M., et al., Nature, vol. 318, pp. 385–388 (1985).
Young, D., et al., Cell, vol. 45, pp. 711–719 (1986).
Gimenez-Gallego, G., et al., *Science*, vol. 230, pp. 1385–1388 (1985).

*Primary Examiner*—Richard A. Schwartz
*Assistant Examiner*—S. L. Nolan
*Attorney, Agent, or Firm*—John P. White

[57] ABSTRACT

This invention provides a purified polypeptide having growth factor activity and a defined amino acid sequence. The invention also provides a purified nucleic acid molecule encoding the polypeptide. This invention further provides methods for producing the polypeptide as well as uses thereof. Finally, this invention provides methods for detecting the polypeptide.

3 Claims, 12 Drawing Sheets

Figure 7

```
GGCCTCTCCCCTTCTCTTCCCCGAGGCTATGTCCACCCGGTGCGGCGAGGCGGGCAGAGCAGAGGC

ACGCAGCCGCACAGGGGCTACAGAGCCCAGAATCAGCCCTACAAGATGCACTTAGGACCCCCGCGG
                    M   S   L   S   F   L   L   L   F   F   S   H   I   L   S   A   W
CTGGAAGAATGAGCTTGTCCTTCCTCCTCCTCTTCTTCAGCCACCTGATCCTCAGCGCCTGGG

A   H   G   E   K   R   L   A   P   K   G   Q   P   G   P   A   A   T   D   R   N   P
CTCACGGGGAGAAGCGTCTCGCCCCCAAAGGGCAACCCGGACCCGCTGCCACTGATAGGAACCCTA

I   G   S   S   S   R   Q   S   S   S   S   A   M   S   S   S   S   A   S   S   S   P
TAGGCTCCAGCAGCAGACAGAGCAGCAGTAGCGCTATGTCTTCCTCTTCTGCCTCCTCCTCCCCCG

A   A   S   L   G   S   Q   G   S   G   L   E   Q   S   S   F   Q   W   S   L   G   A
CAGCTTCTCTGGGCAGCCAAGGAAGTGGCTTGGAGCAGAGCAGTTTCCAGTGGAGCCTCGGGGCGC

R   T   G   S   L   Y   C   R   V   G   I   G   F   H   L   Q   I   Y   P   D   G   K
GGACCGGCAGCCTCTACTGCAGAGTGGGCATCGGTTTCCATCTGCAGATCTACCCGGATGGCAAAG

V   N   G   S   H   E   A   N   M   L   S   V   L   E   I   F   A   V   S   Q   G   I
TCAATGGATCCCACGAAGCCAATATGTTAAGTGTTTTGGAAATATTTGCTGTGTCTCAGGGGATTG

V   G   I   R   G   V   F   S   N   K   F   L   A   M   S   K   K   G   K   L   H   A
TAGGAATACGAGGAGTTTTCAGCAACAAATTTTTAGCGATGTCAAAAAAAGGAAAACTCCATGCAA

S   A   K   F   T   D   D   C   K   F   R   E   R   F   Q   E   N   S   Y   N   T   Y
GTGCCAAGTTCACAGATGACTGCAAGTTCAGGGAGCGTTTTCAAGAAAATAGCTATAATACCTATG

A   S   A   I   H   R   T   E   K   T   G   R   E   W   Y   V   A   L   N   K   R   G
CCTCAGCAATACATAGAACTGAAAAAACAGGGCGGGAGTGGTATGTTGCCCTGAATAAAAGAGGAA

K   A   K   R   G   C   S   P   R   V   K   P   Q   H   I   S   T   H   F   L   P   R
AAGCCAAACGAGGGTGCAGCCCCCGGGTTAAACCCCAGCATATCTCTACCCATTTTCTTCCAAGAT

F   K   Q   S   E   Q   P   E   L   S   F   T   V   T   V   P   E   K   K   N   P   P
TCAAGCAGTCGGAGCAGCCAGAACTTTCTTTCACGGTTACTGTTCCTGAAAAGAAAAATCCACCTA

S   P   I   K   S   K   I   P   L   S   A   P   R   K   N   T   N   S   V   K   Y   R
GCCCTATCAAGTCAAAGATTCCCCTTTCTGCACCTCGGAAAAATACCAACTCAGTGAAATACAGAC

L   K   F   R   F   G  end
TCAAGTTTCGCTTTGGATAATATTAATCTTGGCCTTGTGAGAAACCATTCTTTCCCCTCAGGAGTT

TCTATAGGTGTCTTCAGAGTTCTGAAGAAAAATTACTGGACACAGCTTCAGCTATACTTACACTGT

ATTGAAGTCACGTCATTTGTTTCAGTGTGACTGAAACAAAATGTTTTTTGATAGGAAGGAAACTG
```

FIGURE 8-1

```
FGF-3   (1)   M S L S F L L L F F S H L I L S A W A   (20)
hst     (1)   M S G P G T A A V A L L P A V L         (16)

FGF-3   (21)  H G E K R L A P K G Q P G P A A T D R N  (40)
hst     (17)  L A L L A P W A G R G G A A A P T A P N  (36)

FGF-3   (41)  P R G S S S R Q S S S S A M S S S S A S  (60)
hst     (37)  G T L E A E L E R R W E S L V A L S L A  (56)
int-2   (1)                   M G L I W L L L S L L E P S W P T  (18)
bFGF    (1)                                           M A       (2)

FGF-3   (61)  S S P A A S L G S Q G S G L E Q S S F Q  (80)
hst     (57)  R L P V A A Q P K E A A V Q S G A G D Y  (76)
int-2   (19) T G P G T R L R R D A G G R G G V Y E H  (38)
bFGF    (3)  A G S I T T L P A L P E D G G S G A F P  (22)
aFGF    (1)  M A E G E I T T F T A L T E K F N L P    (19)
```

FIGURE 8-2

```
FGF-3  (81)  WSLGARTGSLYCRVGIGFHL  (100)
hst    (77)  LLGIKRLRRLYCNVGIGFHL  (96)
int-2  (39)  LGGAPRRRKLYCATK-IYHL  (56)
bFGF   (23)  PGHFKDPKRLYCKNG-GFFL  (41)
aFGF   (20)  LGNYKKPKLLYCSNG-GYFL  (38)

FGF-3  (101) QIYPDGKVNGSHEANMLSV-  (119)
hst    (97)  QALPDGRIGGAHADTRDSL-  (115)
int-2  (57)  QLHPSGRVQGSLENSAYSI-  (75)
bFGF   (42)  RIHPDGRVDGVREKSDPHIK  (61)
aFGF   (39)  RILPDGTVDGTKDRSDQHIQ  (58)

FGF-3  (120) LEIFAVSQGIVGIRGVFSNK  (139)
hst    (116) LELSPVERGVVSIFGVASRF  (135)
int-2  (76)  LEITAVEVGVVAIKGLFSGR  (95)
bFGF   (62)  LQLQAEERGVVSIKGVCANR  (81)
aFGF   (59)  LQLCAESIGEVYIKSTETGQ  (78)
```

FIGURE 8-3

```
              :  :  :  =  :  :  :  :  =  :  :  =  :  :  :  =  :  =  :  :
FGF-3 (140)   F  L  A  M  S  K  K  G  K  L  H  A  S  A  K  F  T  D  D  C   (159)
hst   (136)   F  V  A  M  S  K  .  G  K  L  Y  G  S  P  F  F  T  D  E  C   (155)
int-2  (96)   Y  L  A  M  N  K  R  G  R  L  Y  A  S  D  H  Y  N  A  E  C   (115)
bFGF   (82)   Y  L  A  M  K  E  D  G  R  L  L  A  S  K  C  V  T  D  E  C   (101)
aFGF   (79)   F  L  A  M  D  T  D  G  L  L  Y  G  S  Q  T  P  N  E  E  C   (98)

=  :  :  :  :  :  :  =  :  :  :  :  :  =  :  :  :  :  :  :
FGF-3 (160)   K  F  R  E  R  F  Q  E  N  S  Y  N  T  Y  A  S  A  I  H  R   (179)
hst   (156)   T  F  K  E  I  L  L  P  N  N  Y  N  A  Y  E  S  Y  K  Y  P   (175)
int-2 (116)   E  F  V  E  R  I  H  E  L  G  Y  N  T  Y  A  S  R  L  Y  R   (135)
bFGF  (102)   F  F  F  E  R  L  E  S  N  N  Y  N  T  Y  R  S  R  K  Y  S   (121)
aFGF   (99)   L  F  L  E  R  L  E  E  N  H  Y  N  T  Y  I  S  K  K  H  A   (118)

:  :  :  :  :  :  :  :  :  :  :  :  :  :  :  :  :  :  :  :
FGF-3 (180)   T  E  K  T  G  R  E  -  -  -  -  -  -  -  -  -  W  Y  V      (189)
hst   (176)   G  -  -  -  -  -  -  -  -  -  -  -  -  -  -  -  M  F  I      (179)
int-2 (136)   T  G  S  S  G  P  G  A  Q  R  Q  P  G  A  Q  R  P  W  Y  V    (155)
bFGF  (122)   S  -  -  -  -  -  -  -  -  -  -  -  -  -  -  -  W  Y  V      (125)
aFGF  (119)   E  K  H  -  -  -  -  -  -  -  -  -  -  -  -  -  W  F  V      (124)
```

FIGURE 8-4

```
FGF-3 (190) ..ALNKRGKAKRGCS--..SPRVKPQH (209)
hst   (180)   ALSKNGKTKKG--I--..NRVSPTM-Q (197)
int-2 (156)   SVNGKGRPRRG--I--..TRRT--IQ (171)
bFGF  (126)   ALKRTGQYKLG--I--..PKTGPGQ  (143)
aFGF  (125)   GLKKNGRSKLG--I--..PRTHFGQ  (142)

FGF-3 (210) ..ISTHFLPRFKQSEQPELSFT (229)
hst   (198)   KVTHFLPRL*           (206)
int-2 (172)   KSSLFLPRVLGHKDHEMVRL (191)
bFGF  (144)   KAILFLPMSAKS*        (155)
aFGF  (143)   KAILFLPLPVSSD*       (155)

FGF-3 (230) VTVPEKKNPPSPIKSKIPLS (249)
int-2 (192) LNSSQPRAPGEGSQPRQKKQ (211)
```

FIGURE 8-5

```
FGF-3   (250)  A P R K N T N S V K Y R L K F R F G *  (267)
int-2   (212)  S P G D H G K M E T L S T R A T P S T Q  (231)

int-2   (232)  L H T G G L A V A *  (240)
```

ONGOGENE ENCODING POLYPEPTIDE HAVING GROWTH FACTOR ACTIVITY

BACKGROUND OF THE INVENTION

Throughout this application various publications are referenced by numbers within parentheses. Full citations for these publications may be found at the end of the specification immediately preceding the claims. The disclosures of these publications in their entireties are hereby incorporated by reference into this application in order to more fully describe the state of the art to which this invention pertains.

DNA-mediated gene transfer (DNA transfection) into NIH 3T3 murine fibroblast cells has been a fruitful means for detecting oncogenes in mammalian cellular DNA. The most extensively used transformation assay is the NIH 3T3 focus assay, in which transformed 3T3 cells are detected by their growth into dense foci (1). The focus assay has detected activated oncogenes in the genomes of many tumors and tumor-derived cell lines (2-6). The detected oncogenes are usually members of the ras gene family (5-11), although other genes have been characterized as well (5, 12-15). The alternative oncogene assay monitors tumor formation in immunodeficient mice following injection with transfected NIH 3T3 cells. The oncogenes met (16) and mas (17) were discovered by this method.

This invention discloses the use of a new transformation assay to detect a novel oncogene in DNA from human tumor-derived cell lines. The amino acid sequence encoded by the cDNA of this oncogene shows substantial homology to the previously characterized fibroblast growth factors, bFGF and aFGF (40,41), as well as to the amino acid sequence of two recently characterized oncogenes, int-2 and hst (42,43).

SUMMARY OF THE INVENTION

This invention provides a purified polypeptide having growth factor activity and the amino acid sequence shown in FIG. 7. This invention also provides a purified nucleic acid molecule encoding the polypeptide.

This invention further provides a vector which comprises the nucleic acid molecule encoding the polypeptide as well as a host vector system for producing the polypeptide.

This invention also provides a pharmaceutical composition comprising an effective amount of the polypeptide shown in FIG. 7 and pharmaceutically acceptable carrier. The invention further provides a method of stimulating the proliferation of mesodermal cells, capillary growth and promoting tissue repair by administering an effective amount of the pharmaceutical composition.

This invention also provides a fragment of total human genomic DNA comprising the oncogene designated fgf-3. Additionally, this invention provides a molecule useful as a probe for detecting the oncogene.

This invention still further provides a reagent capable of specifically forming a complex with the polypeptide of this invention and a method for diagnosing a neoplastic condition associated with the presence of an activated oncogene.

BRIEF DESCRIPTION OF THE FIGURES

FIG. 7 shows the cDNA nucleotide sequence and the amino acid sequence of the oncogene fgf-3.

FIG. 8 shows a comparison of the fgf-3 oncogene-encoded amino acid sequence to the amino acid sequences for aFGF, bFGF, hst and int-3.

DETAILED DESCRIPTION OF THE INVENTION

Figure 1:
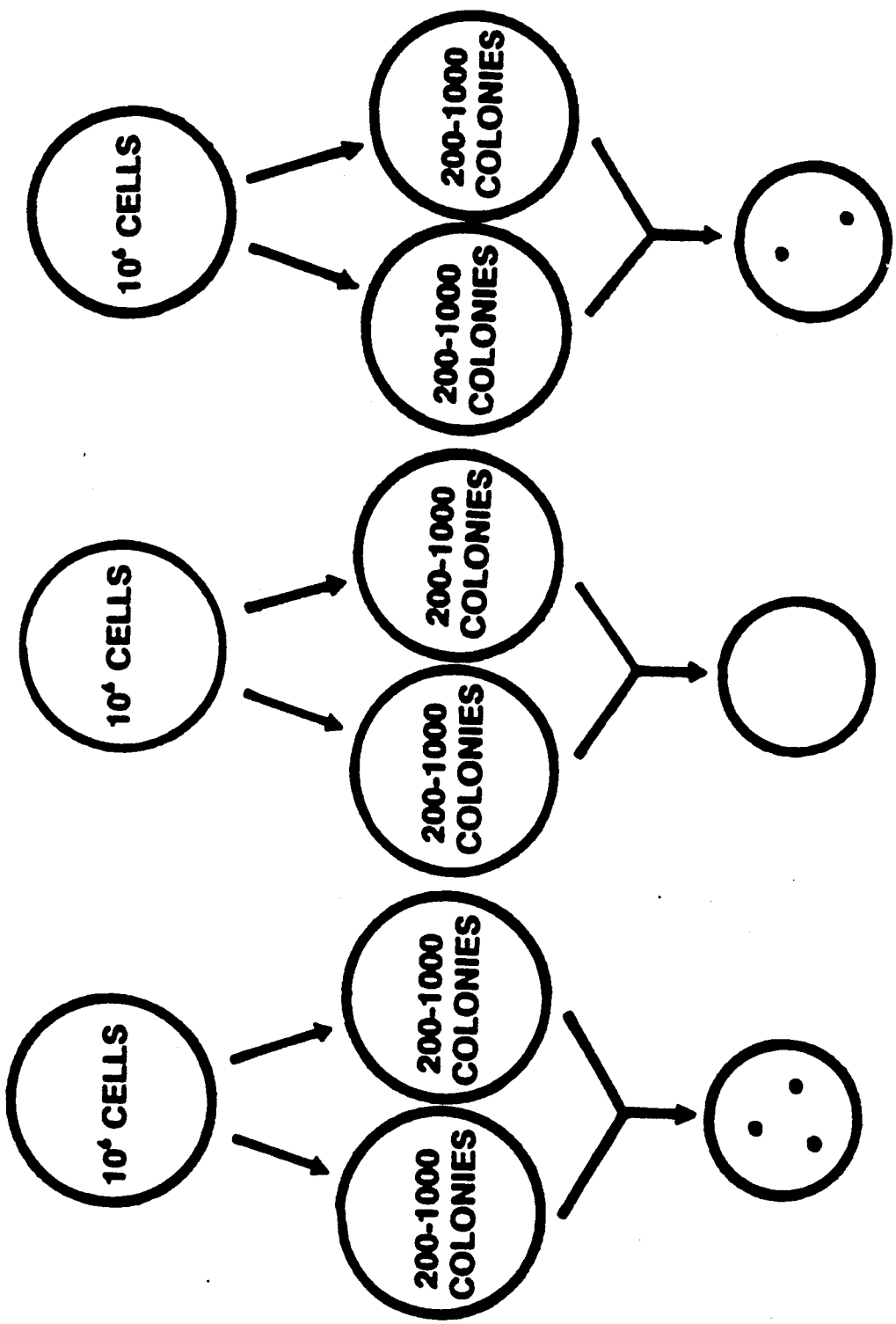
FIG. 1 shows a protocol for detecting oncogenes by defined medium culture. The steps include: 1) Transfect each 100 mm plate with 30 micrograms tumor DNA+1 microgram pLTRneo. 8 hr. 2) Refeed with DME+serum.O/N. 3) Trypsinize. Split 1:2. 4) DME+serum+G418. 12 Days. 5) Trypsinize. 6) Plate $10^5$ cells on fibronectin coated 35 mm dish. Refeed and maintain in defined medium w/o PDGF/FGF. 7) 8 days.

This invention provides a purified polypeptide having the amino acid sequence shown in FIG. 7 and a purified nucleic acid molecule encoding the polypeptide. The nucleic acid molecule may be DNA or RNA.

This invention also provides a vector which comprises the nucleic acid molecule of this invention. This vector may be any vector known in the art including a plasmid or a virus. In a preferred embodiment, the plasmid is designated pLTR-122 and is deposited in an *E. coli* strain under ATCC No. 67413.

This invention also provides a host vector system for producing a polypeptide having the amino acid sequence shown in FIG. 7. The vector comprises a plasmid in a suitable host. The suitable host may be a eucaryotic cell which in turn may be a mammalian cell. Preferably, the mammalian cell is a NIH 3T3 cell.

This invention further provides a method for producing a polypeptide having the amino acid sequence shown in FIG. 7. The method comprises growing the host vector system of this invention so as to produce the polypeptide in the host and recovering the polypeptide so produced.

This invention still further provides a pharmaceutical composition comprising an effective amount of the polypeptide having the amino acid sequence shown in FIG. 7 and a pharmaceutically acceptable carrier. A method of stimulating the proliferation of mesodermal cells is also provided. This method comprises contacting the mesodermal cells with an effective mesodermal cell proliferating amount of the composition of the pharmaceutical composition. In a preferred embodiment the mesodermal cells are vascular endothelial cells. Additionally, the invention provides a method of stimulating capillary growth comprising contacting the capillaries with an effective capillary stimulating amount of the pharmaceutical composition. Further, a method of promoting tissue repair in a subject with damaged tissue is provided. The method comprises contacting the damaged tissue with an effective tissue repairing amount of the pharmaceutical composition.

This invention also provides a fragment of total human genomic DNA comprising the oncogene designated fgf-3. Additionally, a molecule useful as a probe for detecting the oncogene is provided. This probe may be a polynucleotide or an oligonucleotide.

This invention still further provides a reagent capable of specifically forming a complex with the polypeptide shown in FIG. 7. The reagent is preferably an antibody. The antibody may be a polyclonal antibody or a monoclonal antibody.

A method for diagnosing in a subject a neoplastic condition associated with the presence of an activated oncogene is also provided. The method comprises detecting in the subject the presence of at least a portion of the polypeptide shown in FIG. 7. The subject may be a human being and the detecting may comprise contacting the polypeptide with an antibody which specifically binds to the polypeptide encoded by the activated oncogene to form an antibody-polypeptide complex. The complex so formed is then detected, thereby detecting the presence of the oncogene-encoded polypeptide.

Finally, the invention discloses a method of treating cancer in a subject. The method comprises administering to the subject an effective cancer treating amount of the antibody of this invention.

Materials and Methods

Human Tumor Cell Lines. Tumor cell lines were generously provided by Dr. Jorgen Fogh at the Sloan-Kettering Institute for Cancer Research, Rye, N.Y. Most of these cell lines have been described (19-24). Calu4 was derived from a small cell lung carcinoma by Dr. J. Fogh, and MDA-MB-453 was derived from a breast carcinoma by Dr. R. Cailleau.

Preparation of Defined Medium. Defined medium was prepared as described previously (18) by adding supplements to a 3:1 mixture of Dulbecco's medium (DME) and Ham's F12 nutrient mixture, and medium was not used beyond one month after preparation. These supplements were 8 mM NaHCO3, 15 mM HEPES pH 7.4, 3 mM histidine, 4 microMolar MnCl2, 10 microMolar ethanolamine, 0.1 microMolar selenous acid (sodium salt), 2 microMolar hydrocortisone, 5 micrograms/ml transferrin, 500 micrograms/ml bovine serum albumin/linoleic acid complex, and 20 micrograms/ml insulin. Medium was prepared in autoclaved, water-rinsed glass bottles that had not been exposed to serum nor detergents, and was transferred with sterile plastic pipets. Medium exposed to certain plastic vessels became toxic to cells, and, when necessary, defined medium was stored exclusively in Corning polystyrene tubes or flasks.

DNA Preparation Methods. Mammalian cell DNAs and bacterial plasmid and bacteriophage DNAs were prepared by standard methods (2,25,26).

DNA Transfection and Defined Medium Selection. DNA transfection and selection for transformed clones followed the scheme illustrated in FIG. 1. NIH 3T3 cells were transfected under standard conditions (27) with 30 micrograms cellular DNA and one microgram of plasmid pLTRneo (18) per 100 mm dish, then passaged 1:2 and cultured in DME with serum plus 1 mg/ml G418 for approximately 12 days to select colonies which had acquired pLTRneo and, by cotransfer (27), the transfected cellular DNA. Colonies on each pair of culture dishes were trypsinized and pooled, and 100,000 cells in DME+serum were plated onto poly-D-lysine/fibronectin coated dishes (Nunc) as previously described (18). After cell attachment, cultures were refed with the defined medium described above. Cultures were refed with the same medium the next day and thereafter on a three day schedule until all normal cells died and transformed colonies, if any, had developed (7-10 days). Transformed colonies were individually trypsinized and expanded in DME plus serum. Transformed cultures were freed of any residual normal cells by replating on fibronectin-coated dishes and maintaining in defined medium.

Plasmids Employed for Nucleic Acid Hybridization. Plasmids were provided by Drs. M. Wigler, P. Besmer, F. Alt, R. Axel, and R. Parker. Plasmid clones employed were human H-ras, N-ras, N-myc, rho, murine c-myc, and viral K-ras, mos, src, fos, sis, ski, myb, rel, fps/fes, raf/mil, fms, erbAB, fgr. Blur-2 contains a human Alu repeat sequence (30), which we cloned into the BamHI site of pSP64 (31) to generate pSP6-Alu.

Filter-blotted DNA Hybridization. DNAs were digested with restriction endonucleases, subjected to agarose gel electrophoresis, and transferred to nitrocellulose filters by the method of Southern (32). DNA probes were radiolabelled with 32P by nick translation (33), and 32P-labelled RNA was transcribed from EcoRI-linearized pSP6-Alu DNA using SP6 polymerase (31). Hybridizations with Sp6-derived Alu repeat sequence probes were conducted at 43 degrees C in the presence of 50% formamide and 10% dextran sulfate (34), while hybridizations with DNA probes were conducted at 70 degrees C. without formamide/dextran sulfate (2).

Filter-blotted RNA Hybridization. Preparations of cytoplasmic RNA (35) were subjected to electrophoresis through formaldehyde agarose gels, transferred to nitrocellulose, and hybridized by standard procedure (34).

Construction and Screening of Genomic DNA and cDNA Libraries in Bacteriophage Lambda. 15 to 20 kilobase pair DNA fragments purified from EcoRI restriction endonuclease digestion of cellular DNAs were ligated to Charon 4A or EMBL3 bacteriophage vectors, packaged into virions, and screened by standard procedure (36, 37). cDNAs were synthesized from polyA+RNA, using RNase and DNA polymerase to synthesize second strands (38). cDNAs were ligated to EcoRI linkers and cloned into bacteriophage Charon 16A.

Tumorigenicity of Transformed Cell Lines. Tumorigencity of transformed cell lines in immunodeficient nude mice followed procedures described elsewhere (39) and outlined in the legend to Table 3.

Construction of Expression Vector. pvcos-7 (obtained from Stephen Goff and Leslie Lobel, Columbia University) is a cosmid with ampicillin resistance, containing a modified Moloney murine leukemia provirus. The provirus has been modified by a deletion of the nucleotide sequence from the Pst1 site (at map position 1.0 kbp) to the Hpa 1 site (at map position 7.6 kbp). An EcoRI linker has been inserted at the cite of the deletion. The pVCOS-7 and the fgf-3 cDNA were both digested with EcoRI. The fgf-3 cDNA was then cloned into the pvcos-7 by standard procedures. The resulting vector was designated pLTR-122. pLTR-122 was then transfected into NIH 3T3 cells by the method described by Wigler et al. (44). The colonies were then trypsinized, pooled and assayed for oncogene transformed cells by a defined medium culture assay (45).

· Results

Defined Medium Transformation Assay. NIH 3T3 cells can grow efficiently in a basal medium supplemented with transferrin, insulin, and fibroblast growth factor (FGF) or platelet-derived growth factor (PDGF), but die in the absence of FGF and PDGF. By contrast, ras-, sis-, src-, and mos-transformed 3T3 cells proliferate in the PDGF/FGF-free defined medium (18). We have developed a transformation assay based upon cell growth in PDGF/FGF-free defined medium (see FIG. 1 and Methods). Culture of 3T3 cells are transfected with cellular DNA and pLTRneo, selected with neomycin analog G418 to enrich for cells with stabily acquired foreign DNA, and then selected in PDGF/FGF-free defined medium.

We have performed transfections with DNAs from seventeen human tumor-derived cell lines, and have used human placental and NIH 3T3 DNAs as negative controls. The results are tabulated in Table 1.

TABLE 1

Selection of Transformed Cells Following Transfection if NIH 3T3 Cells with NDAs from Human Tumor Cell Lines

| Tumor Cell Line | Tissue of Origin | #G418r Colonies Screened | Number of Independent Transformants | Transformants per 10,000 G418r Colonies | Ras Homology |
|---|---|---|---|---|---|
| Calu-4 | Lung | 8,000 | >8 | >10 | K-ras |
| KNS 62 | Lung | 9,500 | 4 | 4.1 | H-ras |
| SAOS-2 | Bone | 15,000 | 4 | 2.7 | None |
| 639 V | Bladder | 15,000 | 2 | 1.3 | K-ras |
| Sk-N-MC | Neural | 29,000 | 4 | 1.3 | None |
| VM-CUB-2 | Bladder | 19,000 | 2 | 1.1 | None |
| SK-MES-1 | Lung | 53,000 | 4 | 0.8 | None |
| SW 1088 | Astrocyte | 22,000 | 1 | 0.5 | None |
| A 172 | Neural | 9,000 | 0 | | |
| BT-20 | Breast | 9,000 | 0 | | |
| HT 1376 | Bladder | 8,000 | 0 | | |
| 5637 | Bladder | 6,500 | 0 | | |
| MCF-7 | Breast | 8,000 | 0 | | |
| SK-HEP-1 | Liver | 7,000 | 0 | | |
| VM-CUB-1 | Bladder | 6,500 | 0 | | |
| IMR-32 | Neural | 9,000 | 0 | | |
| MDA-MB-453 | Breast | 8,000 | 0 | | |
| Nontransformed Cells | | | | | |
| NIH 3T3 | | 95,000 | 0 | <0.1 | |
| Human placenta | | 84,000 | 1 | 0.1 | |

Table 1. NIH 3T3 cells transfected with tumor cell DNA and pLRneo were first selected for G418 resistance in serum-containing medium. The number of G418r colonies were approximated prior to pooling and culturing in PDGF/FGF-free defined medium. Transformed colonies were considered to derive from independent transfection events if they arose on separate defined media dishes. Transformant containing human ras oncogenes are indicated.

DNAs from eight of the tumor cell lines gave transformants upon transfection, with frequencies ranging from greater than ten transformants per 10,000 G418-resistant colonies screened for Calu-4 lung carcinoma DNA to 0.5/10,000 for SW1088 astrocytoma DNA. Transfections with normal human and mouse DNAs have yielded one transformant for 179,000 G418-resistant colonies screened.

DNA was prepared from transformants derived by transfection with human tumor cell line DNAs. These transformant DNAs were used in a second cycle of 3T3 cel transfection, G418 selection, and defined medium selection. As shown in Table 2, most transformant DNAs generated secondary tranformants upon transfection.

TABLE 2

Selection of Transformed Cells Following Transfection of NIH 3T3 Cells with DNAs from Primary Transformant Cell Lines

| Primary Transformant Cell Line | #G418r Colonies Screened | Number of Secondary Transformants | Transformants per 10,000 G418r Colonies |
|---|---|---|---|
| SAOS2-2 | 16,000 | 0 | <1 |
| SAOS2-3 | 5,000 | 2 | 4.0 |
| VMCUB2-1 | 6,500 | 3 | 4.7 |
| VMCUB2-2 | 13,000 | 4 | 3.1 |
| SKNMC-1 | 3,000 | 3 | 10.0 |
| SKNMC-2 | 6,500 | 3 | 4.7 |
| SKNMC-3 | 9,500 | 0 | <1 |
| SKMES-1 | 6,000 | 1 | 1.7 |
| SKMES-2 | 7,000 | 4 | 5.7 |

TABLE 2-continued
Selection of Transformed Cells Following Transfection of NIH 3T3 Cells with DNAs from Primary Transformant Cell Lines

| Primary Transformant Cell Line | #G418r Colonies Screened | Number of Secondary Transformants | Transformants per 10,000 G418r Colonies |
|---|---|---|---|
| SKMES-3 | 8,500 | 3 | 3.6 |

Table 2. Primary transformant cell lines derived from transfection and defined medium selection as listed in Table 1. E.g., VMCUB2-2 derived from transfection with DNA from human tumor cell line VMCUB2. Transfection and selection procedures were as described in Table 1.

In some instances, DNAs from secondary transformants were transfected into 3T3 cells to generate tertiary transformants (data not shown).

Tumorigenicity of Transformed Cell Lines. Seven transformed cell lines which derived from transfection with DNAs from four human tumor cell lines were tested for tumorigenicity. Trypsinized cell suspensions were inoculated into athymic nu/nu (nude) mice, which were monitored for tumor development. As shown in Table 3, six of the seven transformed cell lines were strongly tumorigenic, inducing progressive tumors in all inoculated mice within two weeks.

TABLE 3
Tumorigenicity of Transformed Cell Lines in Nude Mice

| Transformant Inoculated | No. Mice with Tumors/ No. Mice Inoculated | Latency (weeks) |
|---|---|---|
| SAOS2-3-1 | 3/3 | 2 |
| SAOS2-3-1-1 | 3/3 | 1-2 |
| VMCUB2-1-1 | 3/3 | 1-2 |
| VMCUB2-1-2 | 1/3 | 6 |
| SKMES-4 | 3/3 | 1-2 |
| SKMES-5 | 3/3 | 1-2 |
| SKMES-3 | 3/3 | 1-2 |
| NIH 3T3 | 0/3 | No tumors after 11 weeks |

Table 3. Transformed cell lines and normal NIH 3T3 cells were trypsinized, counted, and inoculated subcutaneously into athymic nu/nu mice, as previously described (54). Two million cells were injected per mouse, except for cell lines VMCUB2-1-2 and SKMES-4, for which one million cells were used. Mice were monitored weekly for appearance and progression of tumors at site of inoculation. The latency period is the average period for appearance of progressive tumors.

The seventh transformant was weakly tumorigenic, while normal NIH 3T3 cells were not tumorigenic over the eleven week monitoring period. Hence, the transfected genes which confer growth factor independence also confer oncogenic potential to 3T3 cells.

Figure 2:
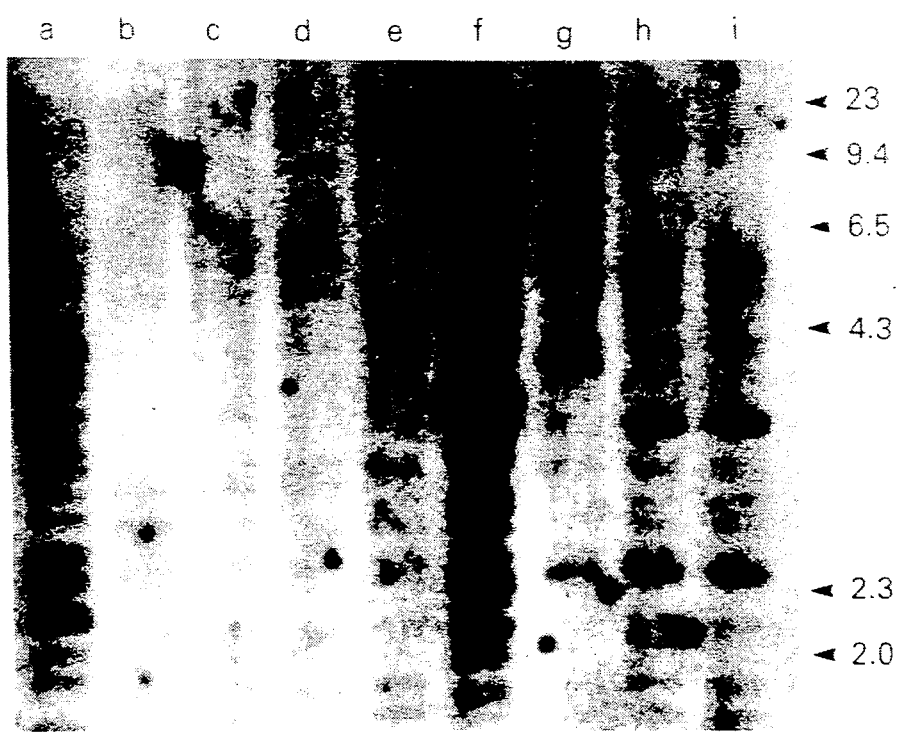
FIG. 2 shows human Alu repeat sequences in transformants derived from VMCUB2 tumor DNA transfections. EcoRI-digested DNAs from primary and secondary transformants of VMCUB2 were analyzed by filter blot hybridization with pSP6-Alu 32P-RNA. DNA from primary transformant VMCUB2-2 (lane a) and its secondary transformants (b-e), primary transformant VMCUB2-1 (f) and its secondary transformants (g-i). Arrows denote size markers (in kbp).

Structure of the Oncogene in a Transformant Derived by Transfection with VMCUB2 Bladder Carcinoma DNA. Four secondary transformants derived from primary transformant VMCUB2-2 lack Alu repeats (FIG. 2, lanes b-e) while three transformants derived from primary VMCUB2-1 each have two Alu sequences (lanes g-i), one of which is within a conserved 2.3 kbp EcoRI DNA fragment. Hence, different molecular events gave rise to the two primary VMCUB2 transformants. The human oncogene in transformant VMCUB2-1 has been cloned from a phage genomic library of secondary transformant VMCUB2-1-1. Initial clones were obtained by Alu sequence homology, and further clones were obtained by genomic walking.

Figure 3:
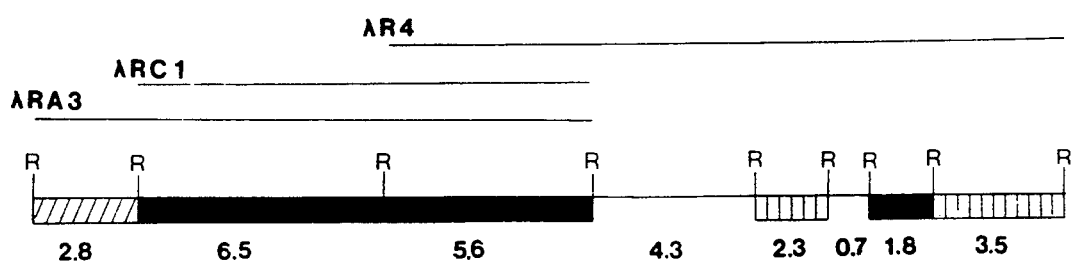
FIG. 3 shows the physical map of the fgf-3 oncogene. The inserts of three overlapping genomic clones are shown. Kilobase pair lengths in kbp) of EcoRI (R) restriction fragments are indicated. Fragments containing Alu repeats are indicated with vertical hashmarks, fragments homologous to the oncogene cDNA clone are indicated as solid boxes, and the 2.8 kbp fragment derived from pLTRneo is marked with diagonal stripes.

A physical map of the fgf-3 oncogene is shown in FIG. 3. The genomic inserts in the RA3 and R4 phage DNA isolated lack transforming activity. However, a ligated mixture of RA3 and R4 partial EcoRI digests gave many transformed colonies following transfection (data not shown). This demonstrates that these two overlapping clones span the entire oncogene. As shown in FIG. 3, three genomic EcoRI fragments in the gene hybridize to a 1.1 kbp cDNA corresponding to the transcript of this gene. This cDNA has transforming activity when fused to a retroviral promoter (Zhan and Goldfarb, manuscript in preparation). We have hybridized this cDNA clone at low stringency to a panel of eighteen known oncogenes and have failed to detect sequence homology.

The coding strand of the cDNA was determined by sequencing the long open reading frame (see below), and the 5'-3' orientation of the genomic DNA map was determined by mapping genomic restriction enzyme sites corresponding to sites on the cDNA.

Surprisingly, we found that the 2.8 kbp EcoRI fragment at the 5' end of the oncogene locus hybridized to the identically sized RI fragment of pLTRneo (FIG. 3). Further mapping of restriction sites at the 5' end of the oncogene allowed us to conclude that transfection of VMCUB2 bladder carcinoma DNA together with pLTRneo had resulted in a fortuitous DNA rearrangement, whereby the LTRneo plasmid became linked to the 5' end of the oncogene in a 5'-5' orientation. The breakpoint between human and plasmid DNAs is located within the 1 kbp region between the XbaI site in LTRneo and the PstI site in the 5' transcribed region of the human gene.

Figure 6:
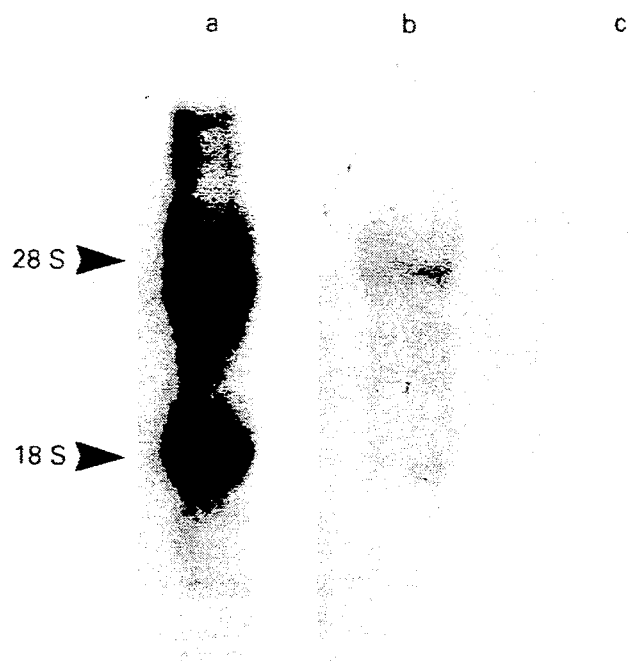
FIG. 6 shows the hybridization of RNAs to the fgf-3 oncogene cDNA probe. Cytoplasmic RNAs (10 micrograms) from secondary transformant VMCUB2-1-1 (lane a), human tumor cell line VMCUB2 (b) and NIH 3T3 cells (c) were analyzed by formaldehyde-agarose gel electrophoresis transfer to nitrocellulose, and hybridization to the 32P-labelled VMCUB2-1 oncogene cDNA. The autoradiogram was exposed 3 hrs (lane a) and 24 hr (lanes b, c). Migration of 18S and 28S rRNAs are indicated.

This rearrangement probably results in increased oncogene expression due to the influence of the retrovirus enhancer element in pLTRneo. This is supported by RNA filter blot analysis, using the oncogene cDNA as hybridization probe. As shown in FIG. 6, the cDNA detects two abundant transcripts (@18S and @28S) in a transformant bearing the fgf-3 oncogene (lane a). This expression is dramatically higher (approximately 50-fold) than that seen in the human bladder carcinoma cell line VMCUB2 (lane b). The sizes of transcripts in the human and transformed cells are approximately the same, suggesting that LTR-enhanced transcription proceeds from the native human promoter(s).

One oncogene cDNA (clone 1-2-2) of 1121 base pairs has been completely sequenced in one direction, and partially in the other. A second somewhat smaller cDNA (clone 7-2-1) has been partially sequenced. Overlapping deletion mutants and restriction fragments of these cDNAs were generated in pUC plasmids and sequenced by the dideoxynucleotide chain termination method, using denatured plasmid templates. The DNA sequence is given in FIG. 7. A large open-reading frame specifying a protein of 214 amino acids is indicated. Near the amino-terminus of this amino acid sequence is a hydrophobic domain that may act as a signal sequence to mediate protein secretion, suggesting that the putative growth factor activity of the fgf-3 protein will be found in the medium of c-fgf3 transformed cell cultures. We have found that such transformed cells do secrete potent growth factor activity.

Computer analysis of the nucleotide coding sequence of the fgf-3 cDNA revealed substantial amino acid homology to acidic fibroblast growth factor (aFGF) and basic fibroblast growth factor (bFGF) (FIG. 8). Additionally, two publications show the nucleotide sequences of two recently characterized oncogenes, termed "int-2" and "hst". The predicted amino acid sequences of these proteins are related to those of aFGF, bFGF, and fgf-3. But, unequivocally, fgf-3 is a novel protein which is a member of a now larger family of related proteins. The amino acid sequences of these five proteins are aligned in FIG. 8. Within a core of approximately 120 residues, 23% of these residues are identical for all five proteins, and within this core, 74% of the amino acid residues of fgf-3 are identical to the corresponding residues in at least one other member of the protein family. The percentages of sequence identity in this core region between fgf-3 and other members of the family are:

| | |
|---|---|
| fgf-3: bFGF | 45% sequence identity |
| fgf-3: aFGF | 41% sequence identity |
| fgf-3: hst | 52% sequence identity |
| fgf-3: int-2 | 50% sequence identity |

Expression of the fgf-3 cDNA. We have linked the fgf-3 cDNA clone to the mammalian expression plasmid vector pvcos-7. This construct, termed pLTR-122, transforms fibroblasts with high efficiency. pLTR-122 has been transfected into NIH 3T3 cells to derive transformants which express the oncogene and secrete the fgf-3 encoded growth factor.

We have further found that NIH 3T3 cells transformed with the activated fgf-3 oncogene or with the pLTR-122 fgf-3 cDNA expression plasmid secrete a growth factor which can stimulate DNA synthesis in quiescent Balb/c fibroblast cells. Applicants contemplate that this growth factor is the fgf-3 protein.

Figure 4:
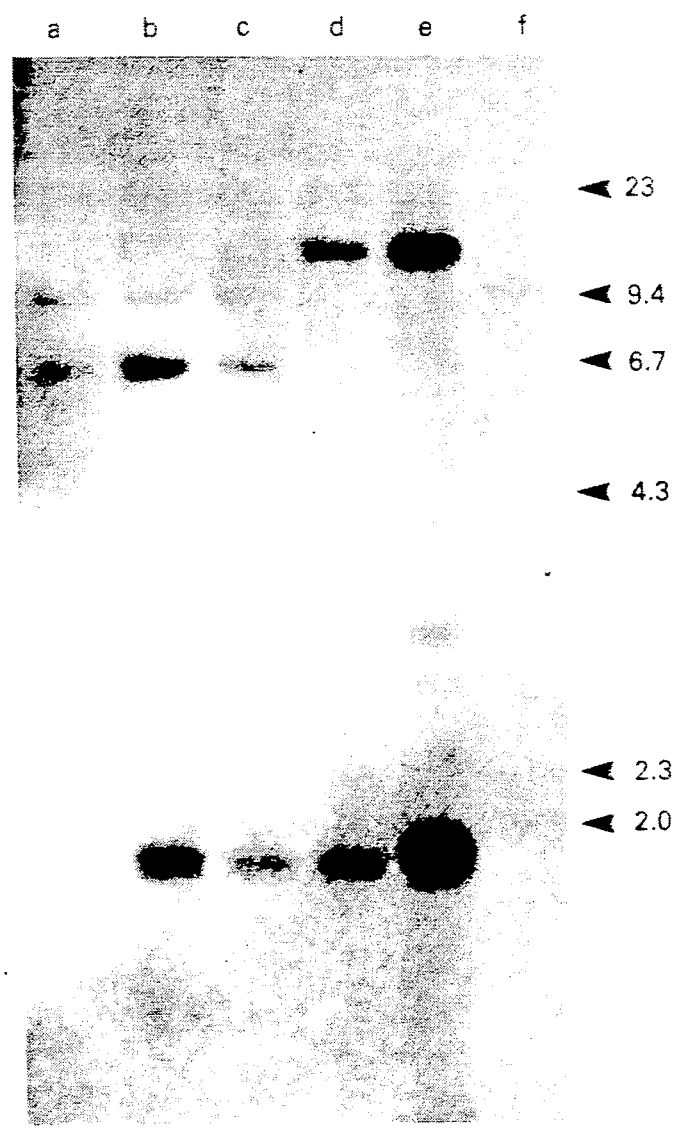
FIG. 4 shows the hybridization of fgf-3 oncogene cDNA clone to genomic DNAs. EcoRI-digested genomic DNAs were analyzed by filter blot hybridization with 32P-labelled 1.1 kbp cDNA corresponding to the oncogene transcripts. DNAs from primary transformants, VMCUB2-1 (lane 9), and its secondary (b) and tertiary (c) transformants, VMCUB 2 human tumor cell line (d), human placenta (e), and NIH 3T3 (f). Arrows denote size markers (in kbp).

Activation of the VMCUB2-1 Oncogene by Transfection-mediated Rearrangement. The VMCUB2-1 oncogene cDNA clone was hybridized to DNAs from VMCUB2 bladder carcinoma cells, human placenta, and 3T3 cells. The cDNA probe detects the 6.5 and 1.8 kbp DNA fragments in the transformants (FIG. 4, lanes a-c), but the probe hybridizes to a 12 kbp fragment instead of the 6.5 kbp segment in human DNAs (lanes d,e). Hence, tranfection of 3T3 cells with VMCUB2 tumor DNA generated the transformant VMCUB2-1 bearing an oncogene with an associated rearrangment.

Figure 5:
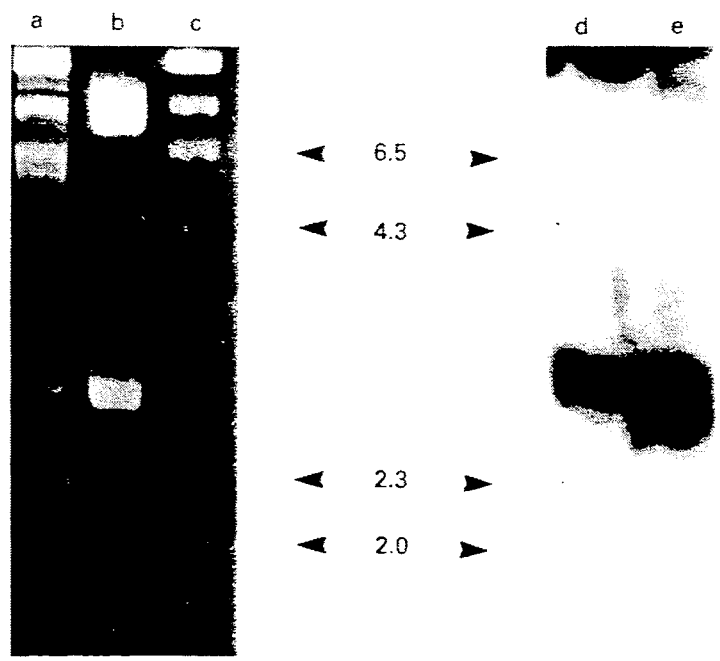
FIG. 5 shows the juxtaposition of fgf-3 oncogene with pLTRneo. DNAs (100 ng) from genomic clone lambda RA3 (lanes a, d) and pLTRneo (lanes b, e) were digested with EcoRI and analyzed by filter blot hybridization, using the 2.8 kbp G418r EcoRI insert of pLTRneo as 32P-labelled probe. The stained gel (lanes a-c) and autoradiogram of the hybridized filter (lanes d, e) show that the RA3 clone contains the G418r insert of pLTRneo. HindIII-digested lambda DNA (lane c) provide size markers.

This observed rearrangment resulted in the fortuitous juxtaposition of pLTRneo with the oncogene, causing dramatic overexpression of the oncogene. FIG. 5 shows that the 2.8 kbp EcoRI DNA fragment flanking the oncogene past the rearrangemnt site is the G418-resistance gene contained in pLTneo. The RNA filter blot hybridization in FIG. 6 shows that expression of the rearranged oncogene in transformed cells (lane a) is at least thirty-fold greater than in the human tumor cell line (lane b). The sizes of the oncogene transcripts are similar in the human and the transformant cell lines, suggesting that the LTR enhancer stimulated transcription of the oncogene from its native promoter(s).

References

1. Shih, C., Shilo, B. Z., Goldfarb, M. P. Dannenberg, A., Weinberg, R. A. (1979) Proc. Natl. Acad, Sci. U.S.A. 76, 5714-5718.
2. Perucho, M., Goldfarb, M. P., Shimizu, K., Lama, C., Fogh, J., Wigler, M. H. (1981). Cell 27, 467-476.
3. Murray, M., Shilo, B., Shih, C., Cowing, D., Hsu, H. W., Weinberg, R. A. (1981) Cell 25, 355-361.
4. Krontiris, T. G., Cooper, G. M. (1981) Proc. Nat. Acad. Sci. U.S.A. 78, 1181-1184.
5. Pulciani, S., Santos, E., Lauver, A. V., Long, L. K., Aaronson, S. A., Barbacid, M. (1983) Nature 300, 539-542.
6. Yuasa, Y., Srivastava, S., Dunn, D. Y., Rhim, J. S., Reddy, E. P., Aaronson, S. A. (1983) Nature 303, 775-779.
7. Parada, L. F., Tabin, C. J., Shih, C., Weinberg, R. A. (1982). Nature 297, 474-475.
8. Santos E., Tronick, S. R., Aaronson, S. A. Pulciani, S., Barbacid, M. (1982) Nature 298, 343-347.
9. Der, C. J., Krontiris, T. G., Cooper, G. M. (1982) Proc Nat. Acad. Sci. U.S.A. 79, 3637-3640.
10. Shimizu, K., Goldfarb, M., Suard, Y., Perucho, M., Li, Y., Kamata, T., Feramisco, J., Stavnezer, E., Fogh, J., Wigler, M. (1983) Proc. Nat. Acad. Sci. U.S.A. 80, 2112-2116.
11. Hall, A., Marshall, C. J. Spurr. N. K., Weiss, R. A. (1983) Nature 303, 396-410.
12. Shimizu, K., Nakatsu, Y., Sekiguchi, M. Hokamura, K., Tanaka, K., Terada, M., Sugimura, T. (1985) Proc. Nat. Acad. Sci. U.S.A. 82, 5641-5645.
13. Fukui, M., Yamamoto, T., Kawai, S., Maruo, K., Toyoshima, K. (1985) Proc. Nat. Acad. Sci. U.S.A. 82, 5954-5958.
14. Eva, A., Aaronson, S. A. (1985) Nature 316, 273-275.
15. Martin-Zanca, D., Hughes, S. H., Barbacid, M. (1986) Nature 319, 743-748.
16. Dean, M., Park, M., LeBeau, M. M., Robins, T. S., Diaz, M. O., Rowley, J. D. Blair, D. G., VandeWoude, G. F. (1985) Nature 318, 385-388.
17. Young, D., Waitches, G., Birchmeier, C., Fasano, O., Wigler, M. (1986) Cell 45, 711-719.
18. Zhan, Z., Goldfarb, M. (1986) Mol. Cell Biol. 6, 3541-3544.
19. Fogh, J. (1978) Nat. Cancer Inst. Monogr. 49, 5-9.
20. Fogh, J., Wright, W. C., Loveless, J. D. (1977) J. Nat. Cancer Inst. 58, 209-214.
21. Fough, J., Fogh, J. M., Orfeo, T. (1977) J. Nat. Cancer Inst. 59, 221-225.
22. Soule, H. D., Vasquez, J., Long, A., Albert, S., Brennan, M. (1973) J. Nat. Cancer Inst. 51, 1409-1416.
23. Takaki, T. (1980) J. Cancer Res. Clin. Oncol. 96, 27-33.
24. Rasheed, S., Gardner, M. B., Rongey, R. W., Nelson-Rees, W. A., Arnstein, P. (1977) J. Nat. Cancer Inst. 58, 881-890.
25. Tanaka, T., Weisblum, B., (1975) J. Bacteriol. 121, 354-362.
26. Yamamoto, K. R., Alberts, B. M., Benzinger, R., Lawhorne, L., Treiber, G. (1970) Virology 40, 734-744.
27. Wigler, M., Sweet, R., Sim, G. K., Wold, B., Pellicer, A., Lacy, E., Maniatis, T., Silverstein, S , Axel, R. (1979) Cell 16, 777-785.
28. Fasano, O., Taparowsky, E., Fiddes, J., Wigler, M., Goldfarb, M. (1983) J. Mol. App. Genet. 2, 173-180.
29. Ellis, R. W., Defeo, D., Shih, T. Y., Gonda, M. A., Young, H. A., Tsuchida, N., Lowy, D. R., Scolnick, E. M. (1981) Nature 292, 506-511.
30. Jelinek, W. R., Tooney, T. P., Leinwand, L., Duncan, C. H., Biro, P., Choudary, A., Weissman, P. V., Rubin, S. M., Houch, C. M. Deninger, P. L., Schmid, C. W. (1980) Proc. Nat. Acad. Sci. U.S.A. 77, 1398-1402.
31. Melton, D. A., Krieg, P. A., Rebagliati, M. R., Maniatis, T., Zinn, K., Green, M. R. (1984) Nuc. Acid Res. 12, 7035-7056.
32. Southern, E. M. (1975) J. Mol. Biol. 98, 503-517.
33. Maniatis, T., Jeffrey, A., Kleid, D. G. (1975) Proc. Nat. Acad. Sci. U.S.A. 72, 1184-1188.
34. Thomas, P. S. (1980) Proc. Nat. Acad. Sci. U.S.A. 77, 5501-5505.

35. Sharp, P. A., Gallimore, P. H., Flint, S. J (1974) Cold Spring Harbor Sympos. Quant. Biol. 39, 457-474.
36. Hohn, B., Murray, K. (1977) Proc. Nat. Acad. Sci. U.S.A. 74, 3259-3263.
37. Benton, W., Davis, R. (1977) Science 196, 180-182.
38. Gubler, U., Hoffman, B. J. (1983) Gene 25, 263-269.
39. Fasano, O., Birbaum, D., Edlund, L., Fogh, J., Wigler, M. (1984) Mol. Cell. Biol. 4:1695-1705.
40. Gimenez-Gallego, G., Rodkey, J., Bennett, C., Rios-Candelore, M., DiSalvo, J., Thomas, K. (1985) Science, 230, 1385-1388.
41. Abraham, J. A., Mergia, A., Whang, J. L., Tumolo, A., Friedman, J., Hjerrild, K. A., Gospodarowicz, D., Fiddes, J. C. (1986) Science, 233, 545-548.
42. Moore, R., Casey, G., Brookes, S., Dixon, M., Peters, G., Dickson, C. (1986) EMBO, 5, 919-924.
43. Taira, M., Yoshida, T., Miyagawa, K., Sakamoto, H. Terada, M., Sugimura, T. (1987) Proc. Nat. Acad. Sci. U.S.A. 84, 2980-2984.
44. Wigler, M., et al. (1979) Cell, 16, 777-785.
45. Zahn, X., Goldfarb, M. (1986) Molecular and Cellular Biology, 6, 3541-3544.

What is claimed is:

1. A purified nucleic acid molecule encoding a polypeptide having an amino acid sequence shown in FIG. 7.

2. The purified nucleic acid of claim 1, wherein the purified nucleic acid is DNA.

3. The purified nucleic acid molecule of claim 1, wherein the nucleic acid molecule is cDNA having a nucleotide sequence shown in FIG. 7.

* * * * *